United States Patent [19]

Huttner et al.

[11] Patent Number: 4,713,057

[45] Date of Patent: Dec. 15, 1987

[54] MECHANICAL ASSIST DEVICE FOR INSERTING CATHETERS

[75] Inventors: James Huttner, Toledo; Marc M. Levine, Sylvania, both of Ohio

[73] Assignee: Medical College of Ohio, Toledo, Ohio

[21] Appl. No.: 583,663

[22] Filed: Feb. 27, 1984

[51] Int. Cl.[4] .............................................. A61M 5/18
[52] U.S. Cl. ..................................... 604/164; 604/264
[58] Field of Search ................... 604/164, 93, 95, 156, 604/264, 198

[56] References Cited

U.S. PATENT DOCUMENTS

| | | |
|---|---|---|
| 2,137,132 | 11/1938 | Cooley . |
| 3,019,790 | 2/1962 | Militana ................................. 604/93 |
| 3,348,544 | 10/1967 | Braun . |
| 3,352,306 | 11/1967 | Hirsch . |
| 3,469,579 | 9/1969 | Hubert . |
| 3,572,334 | 3/1971 | Petterson . |
| 3,685,513 | 8/1972 | Bellamy, Jr. . |
| 3,714,945 | 2/1973 | Stanley . |
| 3,840,008 | 10/1974 | Noiles . |
| 3,906,946 | 9/1975 | Nordstrom . |
| 3,916,892 | 11/1975 | Latham, Jr. . |
| 4,191,186 | 3/1980 | Keeler . |
| 4,193,400 | 3/1980 | Loveless et al. . |
| 4,292,970 | 10/1981 | Hession, Jr. . |
| 4,389,208 | 6/1983 | LeVeen et al. ....................... 604/95 |

Primary Examiner—C. Fred Rosenbaum
Assistant Examiner—Gene B. Kartchner
Attorney, Agent, or Firm—Emch, Schaffer, Schaub & Porcello Co.

[57] ABSTRACT

The application discloses a mechanical assist device for the insertion of a catheter unit into the vein of a patient. The device includes a needle unit, a catheter unit, and a handle member having at least one strut member which engages the catheter unit. The strut member is manually displaced such that the catheter unit is slideably displaced over the needle unit.

11 Claims, 5 Drawing Figures

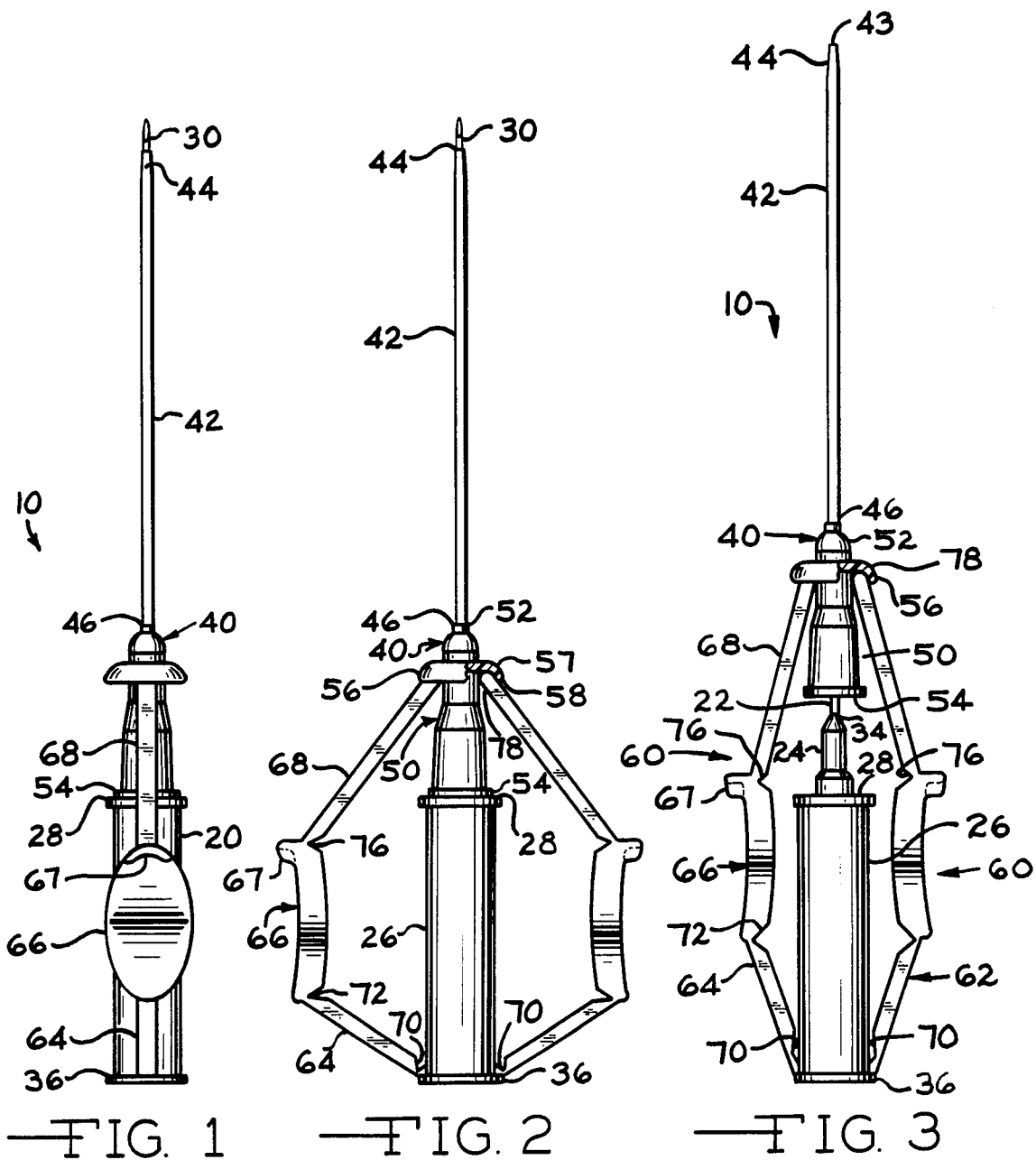

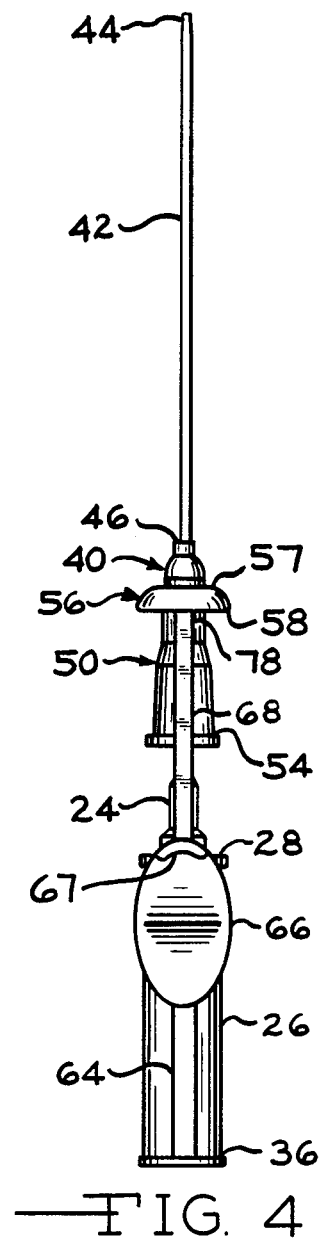
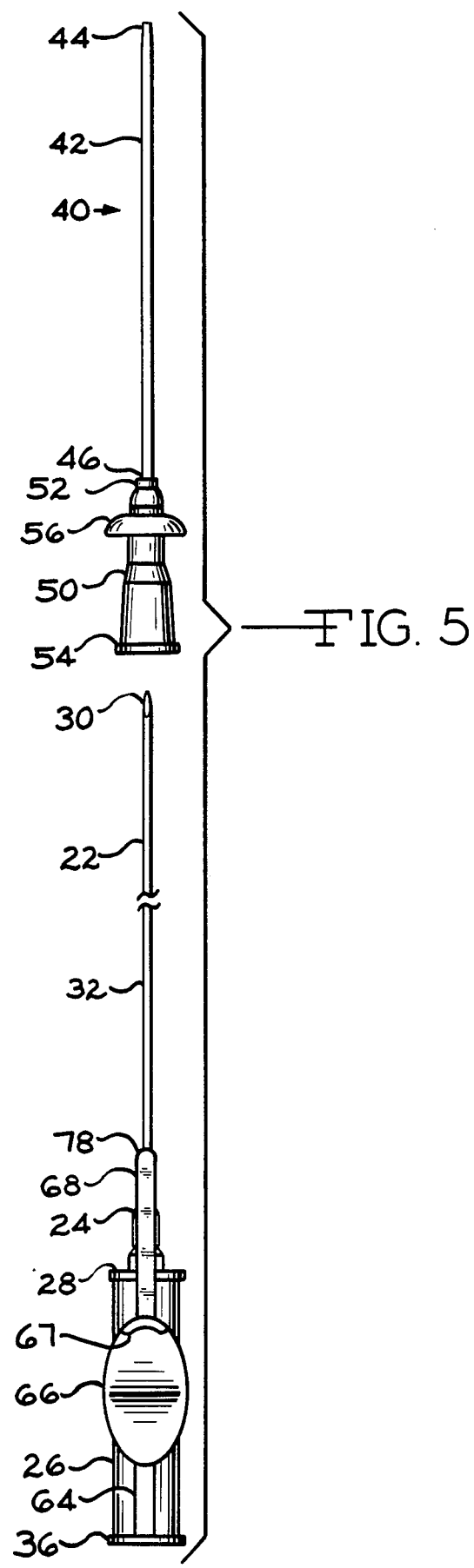

MECHANICAL ASSIST DEVICE FOR INSERTING CATHETERS

BACKGROUND OF THE INVENTION

The present invention relates to a device for use in the insertion of a catheter in the vein of a patient. While the use of catheters is well-known in the medical professions and such use has generally been successful, there are still inherent problems and dangers involved in the insertion of a catheter into the vein of a patient. The insertion of a catheter is an invasive procedure which usually causes some trauma and damage to the vein and the surrounding tissues. Thus, it is incumbent upon the technician to use great care in the insertion of the catheter. However, it is difficult to precisely position the catheter within the vein. Often, the technician does not have adequate control over the advancing end of the catheter insertion device such that the speed and accuracy of the insertion are guaranteed. The technician must use his skills and training to determine when the catheter is being properly positioned while he is advancing the catheter into the vein. Often the needle is accidentally withdrawn from the vein before the catheter is in place. The insertion must be done without damaging or puncturing the opposite side of the vessel wall. The insertion of a catheter into a small vein, such as a child's vein is particularly difficult since the technician's hands are relatively large and the currently available insertion devices are somewhat awkward to use. In addition, the tehnician must be alert for the other possible problems, such as backflow of blood into the catheter device.

Many prior art devices disclose a catheter axially placed over a hypodermic needle. One end of the device is inserted into the vessel wall. The catheter is then manually advanced into the vein while the needle is withdrawn. A major disadvantage to these prior art devices is that this procedure normally requires the use of two hands. Thus, it is difficult for the technician to direct and control the direction of the catheter and simultaneously prevent a backflow of blood into the catheter. Often, a second technician is needed to provide sufficient pressure on the vessel wall to prevent the backflow of blood into the catheter while the first technician guides the catheter into the vein.

Other prior art devices disclose a catheter, axially placed over the hypodermic needle, which can be inserted by using one hand. For example, the Hession, Jr. U.S. Pat. No. 4,292,970 shows a catheter, axially placed over a hypodermic needle, which has a drive plate secured to the hub of the catheter. A quick striking force is delivered to the plate and the catheter is thrust into the vein. The major disadvantage to this prior art is that there is little control or stabilization of the catheter as it is being inserted into the vein. The short, quick jab of the catheter may puncture the vessel wall if it is misplaced. In addition, the relative large drive plate may impede the taping and tie-down procedure for the catheter once the catheter is in place within the vein.

Another prior art apparatus, the Keeler U.S. Pat. No. 4,191,186 shows a catheter axially placed over a hypodermic needle, wherein the catheter is separated from the needle by grasping the needle hub with two or three fingers while simultaneously pushing on a digit engagable means with the thumb or other finger. This prior art often is difficult to manipulate and also requires a rapid movement of the catheter into the vein.

The Stanley U.S. Pat. No. 3,714,945 shows a catheter axially positioned on a hypodermic needle, which also has a digit engagable means extending from the catheter hub. The catheter is advanced by using a thumbnail to push against a protruding flange on the catheter hub. This prior art method requires the action of gripping the needle hub using the entire hand, which is often awkward and unsure, especially when using smaller catheter assemblies.

Thus, there is a need for an improved catheter insertion apparatus to aid in the steady, controlled insertion of a catheter.

There is a further need for an improved catheter insertion apparatus which can be manipulated with one hand.

BRIEF DESCRIPTION OF THE DRAWINGS

FIG. 1 is a side elevation view of an improved catheter insertion apparatus.

FIG. 2 is a front elevation view, partially broken away, showing the catheter insertion apparatus.

FIG. 3 is a front elevation view, partially broken away, showing the catheter insertion apparatus in an extended position.

FIG. 4 is a side elevation view showing the catheter insertion apparatus in the extended position.

FIG. 5 is an exploded side elevation view, showing the catheter member and the catheter insertion apparatus.

SUMMARY OF THE INVENTION

The invention is directed to a means for insertion of a catheter within the vein of a patient. More particularly, the invention relates to a catheter insertion apparatus which can be manipulated with one hand. The catheter insertion apparatus includes a needle system having a hollow needle secured to a hollow chamber in a fluid tight relation. The catheter member is axially positioned on the needle system such that the hub of the catheter is positioned adjacent the hollow chamber. The catheter member includes a flexible shaft which is secured to the catheter hub. The flexible shaft typically is shorter in length than the length of the hollow needle. The catheter hub has a flange or prominent point extending radially from the hub.

A handle member is positioned adjacent the needle system on the catheter member. In a preferred embodiment, the handle member may be integrally molded with the needle system. The handle member includes at least one strut member. One end of the strut member is secured to the end of the chamber member that is opposite the needle. The strut member includes a plurality of segments which are disposed at angles to each other. Each strut segment is operatively attached to the adjacent strut segment. The adjacent strut segments define a hinge or groove. The strut segments are positioned in a longitudinal plane such that they initially extend away from the needle system and then terminate adjacent the needle system. The distal end of the strut member is in touching engagement with the flange member on the catheter hub.

In operation the catheter insertion apparatus is held with one hand. Typically, the fingers are wrapped around the exterior of the strut member. A steady gentle pressure is exerted on the strut member such that the pressure exerted acts to displace the strut segments towards the needle member. The strut segments are extended along the needle member such that the angles between each strut segment are increased. That is, the strut member is displaced to be substantially parallel to the longitudinal axis of the needle system and the catheter member. The distal end of the strut member, which is positioned immediately adjacent the flange member on the catheter hub, pushes against the flange member. The catheter member is axially displaced along the longitudinal axis of the needle system into the vein of the patient in a controlled, stable manner.

It is an object of this invention to provide an improved means for inserting a catheter into the vein of a patient.

It is a further object of this invention to provide an improved means for inserting a catheter into a vein using a single-handed manipulation.

Other objects and advantages of the invention will become apparent as the invention is described hereinafter in detail and with reference to the accompanying drawings.

DESCRIPTION OF THE PREFERRED EMBODIMENT

The invention is directed to a means for placement of a catheter in a vein of a patient. More particularly, the placement means is constructed to facilitate the insertion of the catheter in the vein with minimal damage to the blood vessel wall and the surrounding tissues. The features of the invention will be more fully understood by referring to the attached drawings in connection with the following description of the invention.

The catheter insertion apparatus 10, shown in FIG. 1, is to be used with the conventional intravenous fluid devices for the administration of such parenteral fluids as are prescribed. The catheter insertion apparatus 10 generally includes a needle system 20, a catheter member 40 and a handle system 60. The needle system 20 typically includes a hollow needle 22, a hollow hub member 24, and a hollow chamber member 26. The needle 22 is typically made of a surgical steel. The needle 22 has a sharpened first end 30, a shaft 32 and a second end 34. The second end 34 is suitably secured to the hub member 24. The space defined by the hollow needle 22 is in communication with the space defined by the hollow hub member 24. In a preferred embodiment, the hub member 24 is generally made of a moldable plastic material. The second end 34 is secured in the hub member 24 such that a fluid tight relation exists. The hollow needle 22 and hollow hub member 24 are in communication with the hollow chamber member 26.

The hub member 24 terminates in a shoulder 28. The shoulder 28 defines the end of the chamber member 26 adjacent the hub member 24. The chamber member 26 is generally made of a moldable plastic material and defines an axially extending opening. The opening can operatively receive a syringe, an angiocatheter or a Longdwell, type intravenous catheter. The chamber member 26 is shown as substantially cylindrical in shape, but it should be understood that other shapes can be used without departing from the scope of the invention. The opening in the chamber member 26 is in communication with the hollow space defined by the needle 22.

The catheter member 40 includes a hollow catheter shaft 42 and a catheter hub 50. Catheter shaft 42 is generally made of a flexible surgically compatible, nontoxic material. The catheter shaft 42 has a first, substantially frustoconical end 44 which defines opening 43. The first end 44 tapers or converges towards the opening 43. The catheter shaft 42 has a second end 46 which terminates in the catheter hub 50. The catheter hub 50 is typically made of a substantially rigid plastic material. The catheter hub 50 defines an axially extending opening having a substantialy circular cross section. The second end 46 of the catheter shaft 42 is secured to the first end 52 of the catheter hub 50 by suitable securement means such that a fluid tight relation exists. The hollow catheter hub 50 is in communication with the hollow catheter shaft 42. The catheter hub 50 further includes a flange member 56. The flange member 56 is made of a substantially rigid material and can be formed from the same material as the catheter hub 50. The catheter hub 50 and the flange 56 can be made from a moldable plastic material. The flange member 56 generally extends radially from the exterior of the catheter hub 50. As shown in FIGS. 1–5, the flange 56 can extend substantially around the entire circumference of the catheter hub 50. The flange 56 has a first section 57 which extends from the side of the catheter hub 50 in a substantially perpendicular direction. The flange 56 has a second section 58 which is positioned adjacent the first section 57. The second second 58 is positioned at an acute angle to the first section 57 such that the second section 58 defines a lip on the flange 56.

The catheter member 40 is axially positioned on the needle system 20. The opening in the catheter hub 50 is slightly larger than the outside diameter defined by the needle hub 24. The second end 54 of the catheter 50 is designed to matingly engage with the shoulder 28 of the chamber member 26. The inside diameter of the catheter shaft 42 is slightly larger than the outside diameter of the needle 22 such that the catheter shaft 42 readily fits over the needle 22. The frustoconically shaped first end 44 of the catheter shaft 42 tapers inwardly and has an inside diameter that is approximately equal to the outside diameter of the needle 22 such that there is a snug interference fit between the needle 22 and the first end 44 of the catheter shaft 42. The length of the catheter shaft 42 is shorter that the length of the needle 22 such that the first end 30 of the needle 22 extends beyond the first end 44 of the catheter shaft 42 when the catheter member 40 is axially in position on the needle system 20.

A handle member 60 is positioned on the catheter apparatus 10 to facilitate exerting the necessary force to insert the catheter member 40 into a vein of a patient. The handle member 60 is generally made of a substantially rigid material, such as a hard plastic. In a preferred embodiment, the handle member 60 and the needle system 20 can be molded as a single unit. The handle member 60 includes at least one strut member 62. As shown in FIGS. 2 and 3, there are two strut membes 62 that are positioned on opposed sides of the chamber member 26. The strut member 62 are usually placed in opposed relationship and are spaced equidistance apart on the chamber member 26. Each strut member 62 includes a first segment 64, a second segment 66 and a third segment 68. The first, second and third segments are positioned in substantially the same longitudinal plane. The first end of the first segment 64 is suitably attached to the base portion 36 of the chamber 26. A first hinge 70 is positioned on the end of the first segment 64 adjacent the base portion 36. The hinge 70 usually has a smaller cross-sectional area than the cross-sectional area of the first segment 64. The first segment 64 extends from the base portion 36 at an acute ange.

The second end of the first segment 64 is operatively connected to the first end of the second segment 66. The adjacent ends of the first and second segments 64 and 66 define a second hinge 72. The second segment 66 is positioned at an obtuse angle to the first segment 64 and the second segment 66 is substantially parallel to the longitudinal axis of the chamber 26. The second hinge 72 usually has a smaller cross-sectional area than the cross-sectional areas of the first segment 64 and the second segment 66. The second segment 66 can have a substantially flat or slightly dish-shaped surface, as best seen in FIGS. 2 and 3. In the embodiment shown in the drawings, the second segment 66 has a generally oval shape, but it should be understood that various other shapes may be used without departing from the scope of the invention. An engagement member 67 is positioned on the end of the second segment 66 that is adjacent the third segment 68. The engagement member is disposed for providing a bearing surface for the hand of a user of the catheter insertion apparatus 10. The second segment 66 is operatively connected to the third segment 68. The adjacent ends of the second and third segments 66 and 68 define a third hinge 76. The third hinge 76 usually has a smaller cross-sectional area than the cross-sectional areas of the second segment 66 and the third segment 68. The third segment 68 extends from the second segment 66 at an obtuse angle in a direction towards the needle system 20 and the catheter member 40. The third segment 68 has a second end 78. The second end 78 is positioned in adjacent mating engagement with the flange member 56. The second end 78 rests against the interior surface of the first section 57 and the second section 58 of the flange member 56. The first, second and third hinges can be formed as a groove or crease in the plastic material of the strut member to form a bend or hinge point in the strut member.

In order to insert the catheter member into a vessel wall the catheter insertion apparatus 10 is held in one hand with the thumb on the exterior surface that is spaced apart from the chamber 26 of one of the second segments 66. The fingers are positioned around the exterior of the opposing strut members 62 and the chamber 26. The first end 30 of the needle 22 is then inserted into the patient's vein, in a manner that is well-known. The entire catheter insertion apparatus 10 is then advanced in the direction of the lumen created in the vein by the first end 30 of the needle 22. The fingers and thumb of the hand can be positioned to bear against the engagement members 67 on the second segment 66 to assist in advancing the catheter insertion apparatus 10. As the apparatus 10 is advanced the first end 44 of the catheter member 40 is advanced through the lumen into the vein. The frustoconical shape of the first end 44 allows the first end 44 to be eased through the lumen with minimal damage to the surrounding tissue. Manual pressure is exerted on the second segments 66 of the strut members 62 to advance the strut members 62 toward the chamber 26. Again the fingers and thumb of the hand can bear against the engagement members 67 to assist in advancing the strut members 62 towards the chamber 26. The first, second and third segments 64, 66 and 68 are stubstantially rigid and the first, second and third hinges 70, 72 and 76 allow the strut members 62 to be deformed towards the chamber 26. The pressure on the strut members 62 causes the first segment 64 and third segment 68 to be substantially parallel to the longitudinal axis of the insertion apparatus 10.

The second ends 78 of the third segments 68 are positioned adjacent the flange member 56. As the strut members 62 are advanced toward the chamber member 26 the second ends 78 push against the flange 56 on the catheter hub 50. The catheter hub 50 and the catheter member 40 are axially displaced along the longitudinal axis of the needle system 20. The first end 44 of the catheter member 40 is advanced to a distance beyond the first end 30 of the needle 22. The catheter member 40 can then be guided further into the vein of the patient, if necessary. The needle system 20 and the handle member 60 can then be removed from the catheter member 40 and the lumen in the vessel wall leaving the catheter member 40 safely inserted in the vein of the patient.

Only one hand is required to hold the catheter insertion apparatus 10 during the insertion of the needle 22 and the first end 44 of the catheter member 40 into the vein. Also, only one hand is required to apply pressure to the strut members 62 to advance the catheter member 40 beyond the first end 30 of the needle 22 so that the catheter member 40 is properly positioned in the vein and the needle system 20 can be removed. Thus, the catheter insertion device of the present invention only requires the use of one hand for effective insertion of a catheter. The single-handed operation of the catheter insertion apparatus 10 allows the other hand to be used to apply the necessary pressure on the area of the lumen in the vessel wall such that there is no backflow of blood into the catheter or for any other required task during the insertion of the catheter. In addition, the apparatus 10 is particularly suited for use in inserting smaller catheters in patients with small veins, especially children.

The above detailed description of the invention is given only for the sake of explanation. Various modifications and substitutions other than those cited can be made without departing from the scope of the invention as defined in the following claims.

What we claim is:

1. Apparatus for the insertion of a catheter comprising:

a needle member, said needle member including a needle having a first end and a second end, said first end of said needle being disposed for insertion into a vein of a patient;

a catheter unit positioned around said needle member, said catheter unit including a hollow catheter member that is movably and axially positioned around said needle, said catheter member having a first end and a second end, said first end of said catheter member terminating adjacent said first end of said needle, said first end of said needle extending from said catheter member; and a handle member operatively connected to said needle member and said catheter unit, said handle member being positioned in adjacent spaced apart relationship with said needle member, said handle member and said needle member being designed to be held in one hand, said handle member includes at least one movable strut member, said strut member having a first end connected to said needle member and a second end positioned adjacent said catheter unit, said strut being moveable in a direction towards said needle member, said strut member includes a first segment extending from said needle member at an acute angle, a second segment connected to said first segment and being positioned in substantially the same longitudinal plane as said first segment, said second segment extending from said first segment at an obtuse angle, said second segment being substantially parallel to the longitudinal axis of said needle member, a third segment connected to said second segment and being positioned in substantially the same longitudinal plane as said first and second segments, said third segment extending from said second segment at an obtuse angle, said third segment extending in a direction towards said catheter unit, said end of said third segment that is spaced apart from said second segment being in engagement with said catheter unit, said first segment includes a first hinge, said hinge being positioned on the end of said first segment that extends from said needle member, said hinge being formed in said first segment and having a smaller cross-sectional area than the cross-sectional area of said first segment, said first hinge designed to allow said first segment to be displaced in a direction towards said needle member, the second end of said first segment and the first end of the second segment defining a second hinge, said second hinge being formed in the juncture of said first and second segments and having a smaller cross-sectional area than the cross-sectional areas of said first and second segments, said second hinge designed to allow said first and second segments to be displaced in a direction toward said needle member, the second end of said second segment and the first end of said third segment defining a third hinge, said third hinge, being formed in the juncture of said second and third segments and having a smaller cross-sectional area than the cross-sectional areas of said second and third segments said third hinge designed to allow said second and third segments to be displaced in a direction towards said needle member, said handle member being deformable towards said needle member whereby said handle member acts upon said catheter to advance said catheter member along said needle whereby said first end of said catheter member is advanced beyond said first end of said needle into said vein of said patient and said needle member and handle member can be removed from said catheter unit to leave said catheter unit operatively positioned in said vein, only one hand being required to position and insert said catheter unit in said vein.

2. The apparatus of claim 4 wherein said first segment includes a first hinge, said hinge being positioned on the end of said first segment that extends from said needle member, said hinge being formed in said first segment and having a smaller cross-sectional area than the cross-sectional area of said first segment, said first hinge designed to allow said first segment to be displaced in a direction towards said needle member, the second end of said first segment and the first end of the second segment defining a second hinge, said second hinge being formed in the juncture of said first and second segments and having a smaller cross-sectional area than the cross-sectional areas of said first and second segments, said second hinge designed to allow said first and second segments to be displaced in a direction toward said needle member, the second end of said second segment and the first end of said third segment defining a third hinge, said third hinge, being formed in the juncture of said second and third segments and having a smaller cross-sectional area than the cross-sectional areas of said second and third segments said third hinge designed to allow said second and third segments to be displaced in a direction towards said needle member.

3. The apparatus of claim 1 wherein said catheter is a hollow tube made of a substantially flexible plastic material, said catheter member having a first end and a second end, said first end having a substantially frustoconical shape, said second end of said catheter tube being suitably secured to a hub member, said hub member including a flange member, said flange member being positioned on the exterior of said hub member.

4. The apparatus of claim 3 wherein said second end of said third segment is in engagement with said flange member on said hub member.

5. The apparatus of claim 4 wherein said handle member is movable from a first position where said second segment is spaced apart from said needle member to a second position where said second segment is positioned adjacent said needle member, in said second position said first and third segments are substantially parallel to and adjacent said needle member, in said second position said second end of said third segment acts against said flange member to advance said catheter member with respect to said needle whereby said first end of said catheter member extends beyond said first end of said needle.

6. The apparatus of claim 5 wherein said flange includes a lip portion, said lip portion being disposed to maintain said second end of said third segment in engagement with said flange.

7. Apparatus for the insertion of a catheter comprising:
a needle member, said needle member including a needle having a first end and a second end, said first end of said needle being disposed for insertion into a vein of a patient;
a catheter unit positioned around said needle member, said catheter unit including a hollow catheter member that is movably and axially positioned around said needle, said catheter member having a first end and a second end, said first end of said catheter member terminating adjacent said first end of said needle, said first end of said needle extending from said catheter member, said hollow catheter member being made of a substantially flexible plastic material, said first end of said catheter member having a substantially frustoconical shape; said catheter unit including a hub member secured to said second end of said catheter member, said hub member including a flange member, said flange member being positioned on the exterior of said hub member;
a handle member operatively connected to said needle member and said catheter unit, said handle member being positioned in adjacent spaced apart relationship with said needle member, said handle member and said needle member being designed to be held in one hand, said handle member being deformable towards said needle member, said handle member including at least one movable strut member, said strut member having a first end connected to said needle member and a second end positioned adjacent said catheter unit, said strut member including a first segment extending from said needle member at an acute angle, a second segment connected to said first segment and being positioned in substantially the same longitudinal plane as said first segment, said second segment extending from said first segment at an obtuse angle, said second segment being substantially parallel to the longitudinal axis of said needle member, an third segment connected to said second segment and being positioned in substantially the same longitudinal plane as said first and second segments, said third segment extending from said second segment at an obtuse angle, said third segment extending in a direction towards said catheter unit, said end of said third segment that is spaced apart from said second segment being in engagement with said catheter unit, said first segment further including a first hinge, said hinge being positioned on the end of said first segment that extends from said needle member, said hinge being formed in said first segment, said first hinge being designed to allow said first segment to be displaced in a direction towards said needle member, the second end of said first segment and the first end of the second segment defining a second hinge, said second hinge being formed in the juncture of said first and second segments, said second hinge being designed to allow said first and second segments to be displaced in a direction toward said needle member, the second end of said second segment and the first end of said third segment defining a third hinge, said third hinge being formed in the juncture of said second and third segments, said third hinge being designed to allow said second and third segments to be displaced in a direction towards said needle member, said second end of said third segment being in engagement with said flange member on said hub member, said handle member being movable from a first position where said second segment is spaced apart from said needle member to a second position where said second segment is positioned adjacent said needle member, in said second position said first and third segments are substantially parallel to and adjacent said needle member and said second end of said third segment acts against said flange member to advance said catheter member with respect to said needle whereby said first end of said catheter member extends beyond said first end of said needle and said needle member, and said handle member can be removed from said catheter unit to leave said catheter unit operatively positioned in said vein, only one hand being required to position and insert said catheter unit in the vein of the patient.

8. The apparatus of claim 7 wherein said flange member further includes a lip portion, said lip portion being disposed to maintain said second end of said third segment in engagement with said flange member.

9. The apparatus of claim 7 wherein said handle member includes at least two strut members, said strut members being positioned in substantially opposed relationship and equidistance apart around said needle member.

10. The apparatus of claim 9 wherein said end of said second segment that is adjacent said third segment includes an engagement member, said engagement member being disposed to provide a bearing surface to assist in advancing said strut members toward said needle member.

11. Apparatus for the insertion of a catheter comprising:
a needle member, said needle member including a needle having a first end and a second end, said first end of said needle being disposed for insertion into a vein of a patient;
a catheter unit positioned around said needle member, said catheter unit including a hollow catheter member that is movably and axially positioned around said needle, said catheter member having a first end and a second end, said first end of said catheter member terminating adjacent said first end of said needle, said first end of said needle extending from said catheter member; and
a handle member operatively connected to said needle member and said catheter unit, said handle member being positioned in adjacent spaced apart relationship with said needle member, said handle member and said needle member being designed to be held in one hand, said handle member includes at least two moveable strut members positioned in substantially opposed relationship and equidistance apart around said needle member, said strut members having a first end connected to said needle member and a second end positioned adjacent said catheter unit, said strut members being movable in a direction towards said needle member, said strut members include a first segment extending from said needle member at an acute angle, a second segment connected to said first segment and being positioned in substantially the same longitudinal plane as said first segment, said second segment extending from said first segment at an obtuse angle, said second segment being substantially parallel to the longitudinal axis of said needle member, a third segment connected to said second segment and being positioned in substantially the same longitudinal plane as said first and second segments, said third segment extending from said second segment at an obtuse angle, said third segment extending in a direction towards said catheter unit, said end of said third segment that is spaced apart from said second segment being in engagement with said catheter unit, said handle member being deformable towards said needle member whereby said handle member acts upon said catheter member to advance said catheter member along said needle whereby said first end of said catheter member is advanced beyond said first end of said needle into said vein of said patient and said needle member and handle member can be removed from said catheter unit to leave said catheter unit operatively positioned in said vein, only one hand being required to position and insert said catheter unit in said vein.

* * * * *